United States Patent
Ringling et al.

(10) Patent No.: US 10,729,586 B2
(45) Date of Patent: Aug. 4, 2020

(54) PLANNING DEVICE FOR AN OPHTHALMIC LASER THERAPY DEVICE

(71) Applicant: Carl Zeiss Meditec AG, Jena (DE)

(72) Inventors: Jens Ringling, Berlin (DE); Delbert Peter Andrews, Oberkochen (DE); Alexander Nikolaev, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 102 days.

(21) Appl. No.: 15/489,229

(22) Filed: Apr. 17, 2017

(65) Prior Publication Data

US 2017/0296386 A1      Oct. 19, 2017

(30) Foreign Application Priority Data

Apr. 19, 2016   (DE) .................... 10 2016 206 581

(51) Int. Cl.
*A61F 9/08*        (2006.01)
*A61F 9/008*       (2006.01)
(Continued)

(52) U.S. Cl.
CPC .......... *A61F 9/00825* (2013.01); *A61B 18/20* (2013.01); *A61B 34/10* (2016.02);
(Continued)

(58) Field of Classification Search
CPC .. A61F 9/008; A61F 9/00802; A61F 9/00804; A61F 9/00812; A61F 9/00814;
(Continued)

(56) References Cited

U.S. PATENT DOCUMENTS

| | | | | |
|---|---|---|---|---|
| 8,920,407 B2* | 12/2014 | Raksi | ...................... | A61F 9/008 606/4 |
| 10,213,339 B2* | 2/2019 | Muehlhoff | .............. | A61F 9/008 |

(Continued)

FOREIGN PATENT DOCUMENTS

WO   WO 2016/058931      4/2016

OTHER PUBLICATIONS

German Search Report for German Application 10 2016 206 581.5 dated Jan. 20, 2017, 14 pages.

(Continued)

*Primary Examiner* — Ahmed M Farah
(74) *Attorney, Agent, or Firm* — Patterson Thuente Pedersen, P.A.

(57) ABSTRACT

A planning device for a scanning pattern of a closed structure in an eye, an ophthalmic laser treatment device and corresponding methods including a scanning pattern of a closed structure in a tissue of a patient's eye in a single-pass method for the control of an ophthalmic laser treatment device, in which a starting point of the macroscopic scanning pattern which contains the scanning pattern is arranged in a region in which the angle between a direction of progress of the macroscopic scanning pattern and a direction of a maximum offset caused by movements of the eye relative to the ophthalmic laser treatment device is minimal, or in a region of a minimum change in the macroscopic scanning pattern (n the z-direction per unit of time, or in a region in which a direction of progress of the macroscopic scanning pattern is parallel to a direction of maximum offset.

26 Claims, 9 Drawing Sheets

(51) Int. Cl.
  *A61B 34/10* (2016.01)
  *A61B 18/20* (2006.01)
  *A61B 18/00* (2006.01)
(52) U.S. Cl.
  CPC ............... *A61B 2018/00601* (2013.01); *A61F 2009/00878* (2013.01); *A61F 2009/00897* (2013.01)
(58) Field of Classification Search
  CPC .............. A61F 9/00825; A61F 9/00827; A61F 9/00834; A61F 2009/00846; A61F 2009/00861; A61F 2009/0087; A61F 2009/00878; A61F 2009/00887; A61F 2009/00891; A61F 2009/00897; A61B 18/20; A61B 2018/2035; A61B 2018/20351; A61B 2018/20355; A61B 2018/00571; A61B 2018/00601; A61B 34/10; A61B 2034/101; A61B 2034/108

USPC .............................. 606/4–5, 10–12; 128/898
  See application file for complete search history.

(56) References Cited

U.S. PATENT DOCUMENTS

2015/0216730 A1* 8/2015 Schuele .............. A61F 9/00834
  606/6
2017/0340483 A1  11/2017 Rill et al.
2018/0193196 A1* 7/2018 Bergt .................. A61F 9/00825

OTHER PUBLICATIONS

English Translated German Search Report for German Application 10 2016 206 581.5, dated Jan. 20, 2017, 14 pages.

* cited by examiner

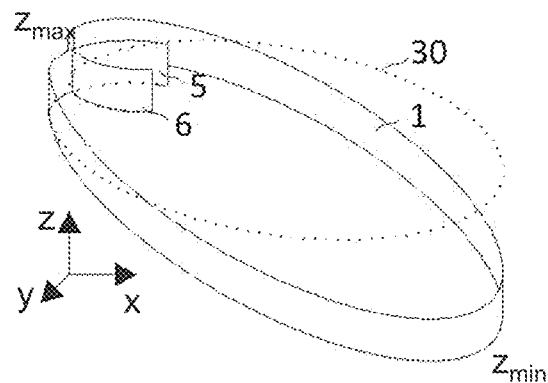
FIG. 8A
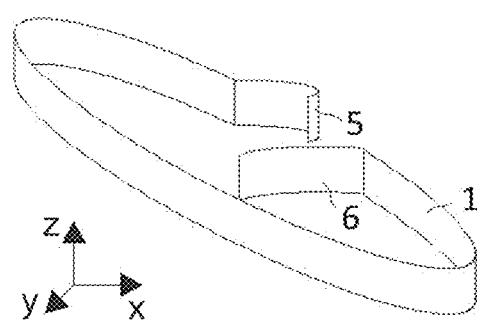
FIG. 8B
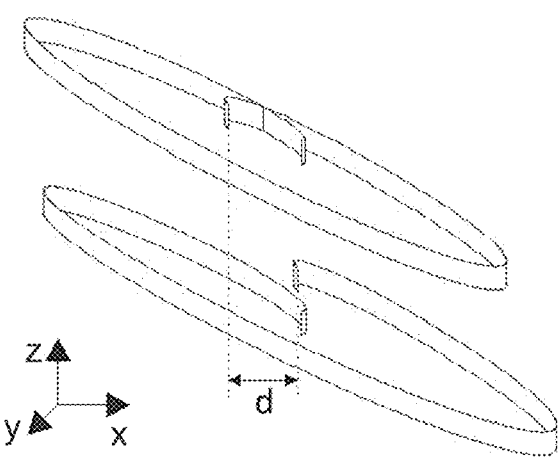
FIG. 8C
FIG. 8D

PLANNING DEVICE FOR AN OPHTHALMIC LASER THERAPY DEVICE

CROSS-REFERENCE TO RELATED APPLICATION

The present application claims priority to German Application No. DE 10 2016 206581.5, filed Apr. 19, 2016, said application being incorporated herein in its entirety by reference.

FIELD OF THE INVENTION

The present invention relates to a planning device for a scanning pattern of a closed structure by the control of an ophthalmic laser treatment device, to produce the closed structure in a tissue of a patient's eye, as well as an ophthalmic laser treatment device with a device for generating a laser beam, an optical system for focusing the laser beam, a device for changing the position of the focus, and a control device. The present invention further relates to a method for planning a scanning pattern of a closed structure for the control of an ophthalmic laser treatment device, and to a method for producing a closed structure in a tissue of a patient's eye.

BACKGROUND

Ophthalmic laser treatment devices are nowadays used in many places for the correction of refractive errors, as well as other eye diseases. In this case, structures are produced in an eye tissue, and can subsequently be extracted, or incisions are made which correct a refractive error by a relaxing effect of the cornea. Detachment symptoms can be corrected. Very often, ophthalmic laser treatment devices are used for cataract surgery, in which the clouded lens of a patient's eye is removed and an intra-ocular lens (IOL) is inserted in its place.

Incision figures generated by a treatment laser beam, by use of photodisruption, are the most frequent applications of an ophthalmic laser treatment device. However, using a treatment laser beam, structures can also be produced by an ablation effect, or otherwise structured tissue changes or tissue adhesions can be produced by a coagulation effect.

During the process of introducing a structure into an eye tissue with a treatment laser beam for example an incision figure made in the cornea, the sclera or the lens and its lens capsule the target can move away from the initial position due to eye movements. The resulting structure then deviates from the planned structure, and is a superimposition of the movement of the focus of the treatment laser beam along a scanning pattern which encodes this structure with the unintended movement of the patient's eye which is being treated.

If at this point, the generation of this structure, in particular an incision figure and/or incision line, begins at a starting point, and the ending point of the generation of the structure by use of the focused treatment laser beam should coincide with this starting point so that a closed structure separates an enclosed volume or an enclosed surface, the result of a movement of the patient's eye being treated is that the starting point and the ending point of the structure no longer meet. If the beginning and the end of an original incision figure no longer meet in a tissue of a patient's eye, the volume within this incision figure is no longer completely separated from the tissue located outside the incision figure. This can be a problem in keratoplasty operations in the cornea, and more particularly in the execution of a capsulotomy incision in cataract operations.

In the case of multi-path incisions, for example, the intended lateral incision figure—that is, the incision figure as can be seen in a top view, is repeated several times successively at slightly varying depths in the target object. In this way, on the one hand, the depth expansion of the target object is covered, a continuous cut is made possible as a result, and deviations in the target object depth and of the cutting depth which are due to tolerances are also bridged. Since different depths of the target object can be produced with different parts of the successively repeated incision figure, if the target object moves, unconnected pieces of the sectioned surface and/or multiple executions of the incision result, because the incision figure is then slightly offset laterally rather than exactly repeated.

FIG. 1A illustrates such a situation in the context of multipath incisions according to the prior art. The sectioned area of the incision FIG. 1 penetrates the incision area 20 along a spatial path. If the sectioned area is composed of incision lines 11 repeated multiple times with a slight vertical offset, or has a helix-like structure, each incision line penetrates the incision area 20 at a vertical height only in a subsector 12 near to the spatial penetration path, and thus effects an incision action there. If, during the incision, there is an offset of the sectioned area, the subsectors 12 have an offset to one another.

FIG. 1B shows various possibilities for the offset of the incision lines in a top view AO of the sectioned area of the incision FIG. 1, and the resulting incision lines of the incision area 20 during the execution of the incision, with lateral offset to the extent of vector u as in the respective figures (i), (ii), (iii). Between the individual subsectors 12, there are gaps as well as overlap, depending on the direction of the offset. The offset positions when a structure is generated in a tissue of a patient's eye are not known a priori.

In the case of single-path incisions according to the prior art, the intended incision FIG. 1 is produced by a single slow sweep and/or "traverse" of a line which is visible in a top view of the incision FIG. 1, rapidly sweeping over a surface which is inclined with respect to the projection surface of the view most commonly a surface perpendicular to the projection surface along this line. In the prior art, the projection surface corresponds to the lateral plane that is, to a plane perpendicular to the optical axis and the incision figure is executed by rapidly sweeping over a depth range during a slow sweep of the line visible in the top view. As shown in FIG. 2A, the sectioned area of the incision FIG. 1 is constructed from adjacent vertical straight lines 13 along an (incisional) line. In this case, the closed incision figure should be circular in the top view. The straight lines 13 penetrate the incision area 20 only in will partial height sections 14, producing an incision effect in these locations.

Adjacent straight lines 13 are also executed in short time intervals, and therefore have only a small offset if there is a temporally variable offset of the sectioned area 20 during the incision relative to the preceding straight line 13. It is only when the end of the incision line needs to once more meet with the beginning that a total offset that is, the offset which arises between the beginning and the completion of the production of the incision FIG. 1 is noticeable.

Without further measures, therefore, the beginning and end of the incision figure would not coincide if the patient's eye moves, nor if there are movements due to other influences during the use of the ophthalmic laser treatment device. The incision would be incomplete.

FIG. 2B shows a top view AO of such an originally circular incision FIG. 1 as is used, for example, for a capsulotomy of the eye lens. It begins at a starting point 2 and ends at the ending point 3. If the sectioned object does not move during the duration of the incision, a closed incision FIG. 1 results. However, if the object moves during the duration of the incision by the vector u, non-closed incision figures can also occur according to the direction of movement and the inner circular part thereof cannot be removed as intended.

SUMMARY

Embodiments of the present invention describe devices and corresponding methods for the planning and for the execution of a scanning pattern of a closed structure in an ophthalmic laser treatment device which make it possible, even if there are small movements of the patient's eye relative to the ophthalmic laser treatment device during the ophthalmic laser treatment between the starting point and the ending point of the creation of the closed structure, to preserve its closed shape and thus make it possible to tolerate smaller movements.

Embodiments of the invention include a planning device for a scanning pattern of a closed structure for the control of an ophthalmic laser treatment device for producing this closed structure in a tissue of a patient's eye, an ophthalmic laser treatment device, a method for planning a scanning pattern of a closed structure and a method for producing a closed structure with an ophthalmic laser treatment device.

In a planning device for a scanning pattern of a closed structure for the control of an ophthalmic laser treatment device for producing this closed structure in a tissue of a patient's eye in a single-path method, a selection table of scanning patterns and/or an algorithm for creating a scanning pattern of the closed structure is encoded in the same. The selection table provides a plurality of scanning patterns for generating a closed structure, from which a scanning pattern is selected based on the intended structure in the tissue of the patient's eye, and based on characterization data of the patient's eye being treated. The algorithm for creating a scanning pattern of the closed structure produces, in contrast, an individual scanning pattern based on characterization data of the patient's eye being treated and the intended structure in the tissue of the patient's eye.

A closed structure in this case is a structure in which, ideally, the ending point returns to the starting point of the generation of the structure, such that the structure completely encloses an area or a volume. The closed structure will therefore usually be a peripheral surface which encloses a volume of the tissue of the patient's eye, which is thereby separated from the remaining tissue of the patient's eye. Since the objective is usually to remove the tissue within this closed structure from the outside tissue, a depth which is greater than the total height of the affected tissue is often chosen for a peripheral surface: the closed structure is then an incision area which penetrates through the tissue. If this structure has a very small depth, it can be assumed to be a line enclosing an area.

The ophthalmic laser treatment device is controlled by the control of its individual components, such as a device for generating a laser beam, an optical system for focusing the laser beam, and/or a device for changing the position of the focus of the laser beam. For such a control, the planning device plans scanning patterns of corresponding closed structures in tissues of patient's eyes.

The scanning pattern is coded as a function of the coordinates of the focus of the laser beam in the tissue of the patient's eye, and possibly of further control coordinates, and as a function of time that is, as a chronological sequence of focus positions. In this case, for example, the corresponding settings of scanners and/or the sequence of the settings of the scanners for changing the position of the focus during the generation of the closed structure are produced by the focus of the laser beam of the ophthalmic laser treatment device.

The scanning pattern in this case describes the change over time in the position of a focus of a laser beam of the ophthalmic laser treatment device in the tissue of the patient's eye, with reference to the three mutually perpendicular spatial directions x, y and z, the z-direction for example being parallel to an optical axis at the site where the laser beam exits the laser treatment device. The Cartesian coordinates in this case can, of course, also be replaced by polar coordinates. The scanning pattern, which is to be understood without the addition of an adjective in the sense of a microscopic scanning pattern, comprises a macroscopic scanning pattern.

This macroscopic scanning pattern results from the in the top view of a projection surface of the intended closed structure, which passes through the closed structure. The line which is visible in the projection surface is the line which should be slowly swept over during the scanning, and adds to the geometric information about this spatial position of this line the information of the starting point and/or the ending point of the slow sweep of this line. The macroscopic scanning pattern is therefore the path of the scanning pattern in the projection surface.

In this case, the projection surface is a plane perpendicular to the optical axis only in the special case, which, however, covers many closed structures which are simple to produce, and which is an example embodiment: if the closed structure is very oblique in space, then it is very reasonable to select as a projection surface a plane which is not perpendicular to the optical axis, or, for complicated closed structures, to select a curved projection surface, and to describe the macroscopic scanning pattern for this surface.

However, for an only-slightly oblique position of the closed structure, of <20°, for example <10° and in a further example <5°, a projection surface perpendicular to the optical axis, in which the macroscopic scanning pattern is described, is selected as the projection surface.

The scanning pattern in a single-path method is then produced by the focus of the laser beam rapidly sweeping over a surface which is inclined with respect to the projection surface usually a surface perpendicular to the projection surface during the simultaneous, one-time, slow sweeping and/or "traverse" of the macroscopic scanning pattern. The rapid sweep over the surface which is inclined with respect to the projection surface is performed, for example, by an oscillatory movement or by combined oscillatory movements. During this rapid sweep, microscopic single paths, so-called tracks, also called strokes or slashes, are created in the surface which is inclined with respect to the projection surface.

If, for example, a projection surface which is perpendicular to the optical axis is selected, although the closed structure has a slightly oblique position, this can advantageously be compensated for by a rapid sweep over a surface which is not perpendicular to the projection surface, the deviation thereof from a perpendicular position thereby compensating for the slight oblique position.

A single-path method in this case is a method for producing a structure, in particular a closed structure, in a tissue of the patient's eye, in which the structure is produced by a single "traverse" of the macroscopic scanning pattern in conjunction with a rapid wobbling that is, a fast back-and-forth movement of the focus of the laser beam around this macroscopic scanning pattern.

For the special case of a structure whose macroscopic scanning pattern runs in a plane perpendicular to the optical axis, a depth range necessary for the closed structure is covered by a fast scan fraction, for example parallel to the optical axis and for example in an oscillatory motion, during the traverse of the macroscopic scanning pattern. In contrast to a multi-path method, there is no risk of an offset of regions of the closed structure which are superimposed in the depth that is, along the optical axis since these are directly generated successively; in the multi-path method, one piece thereof is produced for each passage in a lateral plane (see above, explanations of FIGS. 1A and 1B).

While the offset cannot be systematically corrected over different depths using a multi-path method, a closed-path structure can be generated reliably in a single-path method if the problem of the offset is solved from a starting point of the scanning pattern of the closed structure to an ending point of the scanning pattern.

According to the invention, the planning device is characterized in that the scanning pattern encoded therein is arranged in such a manner that, and/or the algorithm for generating a scanning pattern creates a scanning pattern in such a manner that a starting point of the macroscopic scanning pattern of the closed-structure is arranged in the tissue of the patient's eye in a region in which an angle between a direction of progress of the macroscopic scanning pattern and a direction of maximum offset caused by movements of the patient's eye relative to the ophthalmic laser treatment device are minimal during an ophthalmic laser treatment.

The term 'starting point' in this case is the beginning of the macroscopic scanning pattern for generating the closed structure; the ending point denotes the end of the macroscopic scanning pattern. The direction of progress of the macroscopic scanning pattern indicates the respective direction of the course of an imaginary scan of the focus on the macroscopic scanning pattern.

For example, the starting point of the macroscopic scanning pattern is located in a region in which a direction of progress of the macroscopic scanning pattern runs along a direction of a maximum offset caused by movements of the patient's eye relative to the ophthalmic laser treatment device during an ophthalmic laser treatment. The angle between a direction of progress of the macroscopic scanning pattern and a direction of a maximum offset caused by movements of the patient's eye relative to the ophthalmic laser treatment device during an ophthalmic laser treatment is therefore zero, provided that this condition is met for the macroscopic scanning pattern of a concrete closed structure and a concrete offset problem.

A movement of the patient's eye relative to the laser treatment device occurs due to known and/or predetermined influences, and/or by unknown influences which are only estimated on orders of magnitude or based on experience such as spontaneous movements, for example which act on the laser treatment device or on the patient's eye and which cause drifting of the patient's eye and/or the ophthalmic laser treatment device. The most important influence in this case is the movement of the patient's eye despite the optional fixation of the patient's eye to the ophthalmic laser treatment device by a patient interface. In this case, for example, it is known that, even in the fixed state, the patient's eye is subject to a "breathing movement" which leads to a substantially greater offset in the x-y plane along an axis which runs from superior to inferior that is, an axis perpendicular to an axis running nasal to temporal since the eye moves upwards and downwards with the breath (Eur J Ophthalmol 2015, 25 (2): 112-118, T. Schultz, S. C. Joachim, I. Tischoff, H. B. Dick: "Histologic evaluation of in vivo femtosecond laser-generated capsulotomies reveals a potential cause for radial capsular tears").

Alternatively or simultaneously, the scanning pattern which according to the invention is encoded in the planning device or generated by means of an algorithm in the planning device contains an overlapping structure in an overlap region at the starting point and/or at an ending point of the macroscopic scanning pattern of the closed structure. Such an overlapping structure can therefore of course be utilized independently for considerations with respect to the starting point of the macroscopic scanning pattern, and is helpful for the reliable generation of a closed structure. The combination of both features i.e. a corresponding selection of the starting point and the use of an overlapping structure again increases the safety, and specifically the probability that the structure is actually closed.

An overlapping structure in this case is a sub-region of the closed structure which increases the probability of an overlap of a starting point with an ending point of the macroscopic scanning pattern.

An offset which arises because of a relative movement of the patient's eye despite the fixation of the patient's eye to the ophthalmic laser treatment device is thus counteracted in this case, by modifying a starting point and an ending point of a macroscopic scanning pattern of a closed structure, such as an incision figure, in such a way that an overlap region is created, and the starting point is placed such that the offset has the least possible influence caused by the relative movement of the patient's eye.

According to example embodiments of the invention, the planning device in particular, if one chooses to consider an offset only in an x-y plane, and to disregard a portion of the offset running in the z-direction, that is to say along the optical axis is characterized in that the scanning pattern encoded therein is arranged in such a manner that, and/or the algorithm used to produce a scanning pattern produces a scanning pattern in such a manner that a starting point of the macroscopic scanning pattern of the closed structure in the tissue of the patient's eye is arranged in a region of a minimum change of the macroscopic scanning pattern in the z-direction per unit of time.

The neglected offset in the z-direction is then bridged by the extension of the scanning pattern in the z-direction. Corresponding wobble and/or oscillation movements in a surface perpendicular to the surface of the macroscopic scanning pattern are then increased in amplitude.

Alternatively, the starting point is arranged in a region in which a direction of progress of the macroscopic scanning pattern is parallel to a direction of a maximum offset in an x-y plane caused by movements of the patient's eye relative to the ophthalmic laser treatment device during an ophthalmic laser treatment.

A starting point in a region in which a direction of progress of the macroscopic scanning pattern runs along a direction of the maximum offset can easily coincide with a starting point in a region of a minimum change in the z-direction. If they do not, however, a decision must be made between the two starting point possibilities.

At the same time, the scanning pattern which is encoded in the planning device, or which can be generated by application of an algorithm in the planning device, according to the invention, can also contain an overlapping structure in an overlap region at the starting point and/or at an ending point of the macroscopic scanning pattern of the closed structure.

Furthermore, in a special example embodiment of the planning device, a starting point of the macroscopic scanning pattern of the closed structure is arranged in a region in which the direction of progress runs parallel to an axis which runs superior to inferior i.e., perpendicular to an axis of the patient's eye which runs nasal to temporal. In this way for example, in the production of the circular incision figure of a capsulotomy, that is to say the opening of the capsule bag of the lens of the patient's eye an offset of the eye, caused by a breathing movement, perpendicular to the nasal-to-temporal axis, is counteracted.

For this purpose, the position of the patient's eye axis which runs nasal to temporal or superior to inferior axis is determined beforehand.

In an alternative specific example embodiment, the starting point of the macroscopic scanning pattern is arranged in a region of a minimum or maximum z-coordinate of the macroscopic scanning pattern of the closed structure. This is particularly advantageous in the case of closed structures running in and/or along a surface which is highly tilted with respect to an x-y plane.

In one example embodiment of the planning device, additional parameters of the laser beam are assigned to the scanning pattern such that, for example, a power of the laser beam for generating the closed structure can be dependent on the respective position of the focus of the laser beam in the tissue of the patient's eye.

Further special example embodiments of the planning device, which can be used alone or in combination with the special example embodiments described above, are characterized by special example embodiments of the overlapping structure.

As such, the overlapping structure can be generated by an advancement of the starting point and/or by an extension of the ending point of the macroscopic scanning pattern beyond the actual location of the ending point. This can be utilized in a particularly advantageous manner for producing a closed structure for which the starting point of its macroscopic scanning pattern is arranged in a region in which the direction of progress of the macroscopic scanning pattern is parallel to the direction of the maximum offset in an x-y plane.

For the generation of a circular capsulotomy incision, for example, the macroscopic scanning pattern of a lateral incision figure can extend beyond 360°, which would be sufficient for the creation of a complete and closed circular figure without an offset caused by a relative movement of the patient's eye, and the first segment, starting from the starting point of the macroscopic scanning pattern, is then repeated once again in a region in which the direction of progress runs parallel to an axis running from superior to inferior. Due to an offset which has its maximum perpendicular to the nasal to temporal axis, parallel but extremely small, the starting point of the macroscopic scanning pattern can be reached by the ending point, even with an offset, without further measures, due to this measure. The angular extension beyond 360° for a circular, closed structure must be 180° $u/\pi/r$, where r is the radius of the circular path and u is the maximum offset due to the movement.

The overlapping structure can for example be produced alternatively, or optionally simultaneously, by broadening the closed structure in the overlap region at the starting point and/or at the ending point of the macroscopic scanning pattern. This is particularly possible by changing a power of the laser beam or by reducing a speed of the change in the position of the focus of the laser beam. Such a change can, for example, take place gradually.

Further possible parameters of the laser beam, as well as of the scanning pattern itself, with which the structure can be broadened in an overlap region are, for example, the laser energy, pulse intervals of a pulsed laser beam, and/or path spacings in the case of an oscillation of the scanning pattern in the z-direction.

In a further alternative, the overlapping structure can be produced by meandering in an overlap region at the starting point and/or at the ending point of the macroscopic scanning pattern.

Extensive possibilities for producing an overlapping structure result from the formation of hook-like regions which point into the closed structure or which point out of the closed structure, in particular with an arc shape, in an overlap region at the starting point and at the ending point of the macroscopic scanning pattern of the closed structure.

In a particular example embodiment of the planning device, which is concerned with the further design of the overlapping structure which is formed by a hook-like region, the hook-like region is formed as a function of the maximum offset to be expected, in particular a maximum offset to be expected in the x-y plane, in particular by virtue of the fact that the hook-like regions are produced by circular arcs, for example by quarter circles, with a radius u which corresponds to the amount of the maximum offset to be expected in the overlap region.

For a circular closed structure, such as the (macroscopic) circular incision figure of a capsulotomy incision, an ideal arc-shaped, hook-like overlapping structure can be determined as follows:

In a sector with the angle $\varepsilon$, the intended circular path around a starting point and/or point of completion of the sectioned circle is replaced by smaller circular sectors that is, the arc-shaped hooks with radius u, wherein u is the offset which must be bridged during the incision. The angular range of the circular sector $\varepsilon$ in which such arc-shaped hooks, which either point into the circle as inner hooks or point out of the circle as outer hooks, are produced, is $\varepsilon=\arcsin(u/r-u)$ and/or $\varepsilon=\arcsin(u/r+u)$.

The arc-shaped hooks then extend over an angular range of 90°+$\varepsilon$ around a central point which is at a distance of r−u and/or r+u from the center of the sectioned circle on the arms of the sector $\varepsilon$. The hooks open into the circle with the same tangents and nestle against the legs of the sector $\varepsilon$.

It is not always advantageous to "push through" a closed structure in one pass. In a particular example embodiment of the planning device, the closed structure is composed of at least two non-closed sub-structures, and thus has at least two overlap regions.

Instead of two such non-closed sub-structures with overlap regions at their starting and ending point, a closed structure can also be formed by a plurality of such non-closed sub-structures. Adjacent non-closed sub-structures overlap in this case in their overlap regions, which can be designed as explained above. In this case, a reasonable number of the non-closed substructures is dependent on the design of the closed structure to be produced.

In an example embodiment of the planning device, the closed structure is determined by characterization data of the patient's eye, in particular structural data of the patient's eye, which is determined by a characterization device. Such a characterization device is connected to the planning device via communication channels, wherein this connection can be realized by means of a cable, or else wirelessly.

Structural data of the patient's eye, such as the location of boundary surfaces, is for example determined by optical coherence tomography (OCT), by Scheimpflug camera, by confocal detection, or by ultrasound.

An ophthalmic laser treatment device includes a device for generating a laser beam, an optical system for focusing the laser beam at a focal point in a processing volume, and a device for changing the position of the focus in the processing volume, which can be described with three generally mutually-perpendicular directions in space x, y and z, wherein the z-direction is for example parallel to an optical axis. A patient's eye and/or a section of a patient's eye can be arranged in the processing volume.

The ophthalmic laser treatment device further comprises a control device for controlling the laser treatment device i.e., for controlling the individual components of the laser treatment device such as the device for generating the laser beam, for focusing and for changing the position of the focus, in particular corresponding scanners to change the focus position of the laser beam in the x, y and z directions. The control device in this case can comprise various control elements, which can also be spatially separated from each other. They are interconnected with each other as well as with the other components of the laser treatment device via communication channels. These communication channels can be constructed by cables, or wirelessly.

According to an example embodiment of the invention, the ophthalmic laser treatment device comprises a planning device as described above for a scanning pattern of a closed structure, in which is encoded a selection table of scanning patterns or an algorithm to create a scanning pattern of a closed structure.

The change over time in the position of the focus of the laser beam in a tissue of a patient's eye in the processing volume, with respect to the three directions in space x, y, z, is described by the scanning pattern.

The scanning pattern or the algorithm for the creation of the scanning pattern is coded in this case in such a manner that a starting point of the macroscopic scanning pattern of the closed structure in the tissue of the patient's eye is arranged in a region in which an angle between a direction of progress of the macroscopic scanning pattern and a direction of a maximum offset caused by movements of the patient's eye relative to the ophthalmic laser treatment device during an ophthalmic laser treatment is minimal.

Particularly if one chooses to consider an offset only in an x-y plane, and to disregard a portion of the offset running in the z-direction, that is to say along the optical axis, and/or to compensate for the same by an increased wobbling and/or oscillating of the focus in the z-direction around the macroscopic scanning pattern, the scanning pattern or the algorithm used to produce a scanning pattern is coded in this case such that a starting point of the macroscopic scanning pattern of the closed structure in the tissue of the patient's eye is arranged in a region of a minimum change of the macroscopic scanning pattern in the z direction per time unit, or is arranged in a region in which a direction of progress of the macroscopic scanning pattern runs parallel to a direction of a maximum offset in an x-y plane caused by movements of the patient's eye relative to the ophthalmic laser treatment device during an ophthalmic laser treatment.

Alternatively or simultaneously, the scanning pattern which according to example embodiments of the invention is encoded in the planning device or generated by means of an algorithm in the planning device contains an overlapping structure in an overlap region at the starting point and/or at an ending point of the macroscopic scanning pattern of the closed structure.

The specific example embodiments of the planning device described above are of course also applicable to the planning device included in the laser treatment device according to the invention, and thus lead to specific example embodiments of the laser treatment device according to the invention.

The planning device can be included, in a particular example embodiment, directly in the control device.

For a laser treatment, a patient's eye is for example fixed by use of a patient interface to the ophthalmic laser treatment device, in particular a laser applicator which comprises the exit point of the treatment laser beam.

Another example embodiment of the invention is an ophthalmic laser treatment device according to the invention which comprises a characterization device for generating characterization data of the patient's eye, for example an optical coherence tomography (OCT) device, a Scheimpflug camera, a confocal detector, or an ultrasound device.

The characterization device transmits the characterization data of the patient's eye to the planning device. This is also performed for example automatically via wired and/or wireless communication channels between the characterization device and the planning device.

The characterization data particularly includes structural parameters of the patient's eye, such as the location of boundary surfaces of the eye structures and/or of tissues of the eye.

In another example embodiment of the ophthalmic laser treatment device, the device for generating a laser beam produces a pulsed laser beam, in particular a femtosecond laser beam, or alternatively a picosecond or attosecond laser beam. The closed structure in this case comprises a closed incision figure. This closed incision figure can be a closed sectioned area by which a volume of a tissue of a patient's eye, located within the closed incisional area, is isolated from the tissue external to the closed sectioned area. If there is a small extension in the z-direction i.e., in the depth the closed sectioned area can be considered as a closed incision line.

Such an incision figure and/or sectioned area is generated by a photodisruption process at the point of focus of the pulsed laser beam.

Other ways of using a pulsed laser beam are to remove a closed structure by ablation and/or to adhere and/or change the tissue within a closed structure by coagulation.

A closed structure which corresponds to a capsulotomy incision characterizes a further example planning device according to the invention, and/or an ophthalmic laser treatment device according to the invention. The term 'capsulotomy' is used in this case to mean the opening of the capsular bag of the lens of a patient's eye.

In a method according to the invention for planning a scanning pattern of a closed structure for the control of an ophthalmic laser treatment device and/or its components for generating this closed structure in a tissue of a patient's eye in a single path method in which the scanning pattern describes the change over time of the position of a focus of a laser beam of the ophthalmic laser treatment device in the tissue of the patient's eye with respect to the three spatial directions x, y, and z, and the scanning pattern includes a macroscopic scanning pattern, the scanning pattern is selected from a selection table of scanning patterns or is created by an algorithm. This is done with the aim of transmitting the selected or created scanning pattern to the control of the ophthalmic laser treatment device.

In this method for planning a scanning pattern, a starting point of the macroscopic scanning pattern of the closed structure in the tissue of the patient's eye is determined in a region in which an angle between a direction of progress of the macroscopic scanning pattern and a direction of a maximum offset caused by movements of the patient's eye relative to the ophthalmic laser treatment device during an ophthalmic laser treatment is minimal.

Alternatively or simultaneously, in this method for planning a scanning pattern, an overlapping structure is produced in an overlap region at the starting point and/or at an ending point of the macroscopic scanning pattern of the closed structure.

Particularly if one chooses to consider an offset only in an x-y plane, and to disregard a portion of the offset running in the z-direction, that is to say along the optical axis, and/or to compensate for the same by an increased wobbling and/or oscillating of the focus as described above, in a method for planning a scanning pattern of a closed structure for the control of an ophthalmic laser treatment device, a starting point of the macroscopic scanning pattern of the closed structure in the tissue of the patient's eye is determined in a region of a minimum change of the macroscopic scanning pattern in the z-direction per unit of time, or in a region in which a direction of progress of the macroscopic scanning pattern is parallel to a direction of a maximum offset in an x-y plane caused by movements of the patient's eye relative to the ophthalmic laser treatment device during an ophthalmic laser treatment.

Usually a choice must be made between the two options. In the specific case in which the starting points according to both considerations are in the same region, the same may certainly coincide. If the starting point which is selected according to the first consideration is located in a region other than the starting point which is selected according to the second consideration, a decision must be made between the two variants of the starting point selection.

At the same time, in this method for planning a scanning pattern in an overlap region at the starting point and/or at an ending point of the macroscopic scanning pattern of the closed structure, an overlapping structure can also be produced.

The starting point of the macroscopic scanning pattern of the closed structure can be located in particular in a region in which the direction of progress of the macroscopic scanning pattern is parallel to an axis of the patient's eye which runs superior to inferior, or in a region of a minimum or maximum z-coordinate of the macroscopic scanning pattern of the closed structure.

In this case, additional parameters of the laser beam can be assigned to the (microscopic) scanning pattern of the closed structure.

An overlapping structure can be generated by an advancement of the starting point and/or by an extension of the ending point of the macroscopic scanning pattern beyond the actual location of the ending point. An overlapping structure can also be a broadening of the closed structure in an overlap region at the starting point and/or at the ending point of the macroscopic scanning pattern, by changing a parameter of the laser beam, in particular by a for example gradual change in a power of the laser beam produced, or by reducing a rate of change of the position of the focus. Also, an overlapping structure can be produced by meandering in an overlap region at the starting point and/or ending point of the macroscopic scanning pattern. Last but not least, an overlapping structure can be produced by n hook-like regions which point into or out of the closed structure in an overlap region at the starting point and at the ending point of the macroscopic scanning pattern of the closed structure.

In particular, the hook-like regions can be generated according to the maximum expected offset, in particular the maximum expected offset in the x-y plane. The hook-like areas in this case can be produced by circular arcs having a radius u, corresponding to the amount of the maximum expected offset in an overlap region.

Also, a closed structure can be formed by at least two non-closed structures, each of which may have overlap regions at their respective starting points and ending points of their macroscopic scanning pattern.

In a specific method for planning a scanning pattern of a closed structure for the control of an ophthalmic laser treatment device, characterization data of the patient's eye is produced, and the characterization data of a patient's eye is taken into account manually or automatically in order to select a scanning pattern from a selection table of scanning patterns or to create a scanning pattern of the closed structure.

A manual incorporation is carried out by an evaluation of the characterization data by a physician or other operator and by selecting a scanning pattern from the selection table based on the characterization data, or by entering individual parameters or a category which leads to the creation of a defined scanning pattern.

In the case of an automated incorporation, the characterization data is processed directly, by a scanning pattern being selected from a selection table or the scanning pattern being created with the characterization data.

Furthermore, it is advantageous if, in a method of planning a scanning pattern of a closed structure for the control of an ophthalmic laser treatment device, a fixation of the patient's eye to an ophthalmic laser treatment device is taken into account.

A fixation of the patient's eye to the ophthalmic laser treatment device is performed, for example, by use of a patient interface, such as a liquid patient interface or a contact lens. If a patient's eye is connected via such a patient interface to the laser treatment device, this patient interface exerts a certain pressure on the eye of the patient, which will change previously determined characterization data of the eye. The introduction of a correction parameter for these purposes can be considered.

In a method according to the invention for generating a closed structure, the scanning pattern of a closed structure is planned with a method for planning a scanning pattern of a closed structure, and the scanning pattern of the closed structure is transmitted to a control device of the ophthalmic laser treatment device, and/or gives the control device access to a planning device containing the planned scanning pattern of the closed structure.

The control device ultimately controls the ophthalmic laser treatment device with the aid of the data from the planning device, such that a focus of a laser beam which is produced in the ophthalmic laser treatment device, and the position of which is continuously changed, produces the closed structure in a tissue of a patient's eye.

The invention is explained using the example of a capsulotomy incision made during cataract surgery utilizing a femtosecond laser, but the invention is not limited to the planning and production of a capsulotomy incision.

BRIEF DESCRIPTION OF THE DRAWINGS

The explanations are given with reference to example embodiments, wherein:

FIG. 8A depicts a capsulotomy incision which is not parallel to an x-y plane, which includes an overlapping structure which is formed by inner hooks in an overlap region, and a starting and ending point of the macroscopic scanning pattern at a maximum z-coordinate of the scanning pattern of the capsulotomy incision;

FIGS. 8B, 8C and 8D depicts a capsulotomy incision which is not parallel to an x-y plane, which includes an overlapping structure which is formed by inner hooks in an overlap region, and a starting and ending point of the macroscopic scanning pattern at a position of the maximum change in the z-direction per unit of time.

DETAILED DESCRIPTION

Figure 3:
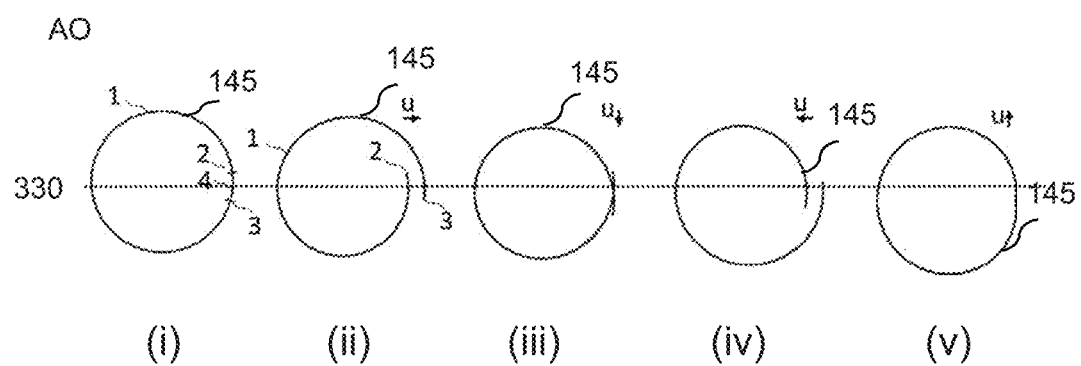
FIG. 3 depicts a capsulotomy incision having its starting point of the macroscopic scanning pattern on a nasal-to-temporal axis, and whose ending point has been extended beyond the initial ending point (the circular incision was therefore made more than 360°), and the effects of different offset directions.

FIG. 3 illustrates a circular capsulotomy incision 1, wherein the starting point 2 of its macroscopic scanning pattern 145 is arranged in a region in which the direction of progress of the macroscopic scanning pattern 145 is parallel to a direction running superior to inferior, but which has been somewhat advanced such that the original starting point is only cut later, and its ending point 3 has been extended beyond the original ending point, and thus the circular incision was executed over more than 360°. The effects of various offset situations for a capsulotomy incision 1 carried out under these conditions are also shown.

Without movement of the target object that is, the patient's eye 310 an overlap region 4 would arise on the desired path of the capsulotomy incision 1, as shown in FIG. 3 (i). As a result of this overlap region 4, the incision line of the capsulotomy incision 1 now remains closed when there is an offset u due to a movement upward or downward i.e., parallel to the axis running superior to inferior, that is, perpendicular to the axis 330 running nasal to temporal as shown in FIGS. 3 (iii) and (v).

However, in the same initial situation, but with a movement of the patient's eye 310 relative to the ophthalmic laser treatment device in the direction of the nose or in the direction of the patient's temple, which generates a maximum offset u parallel to the axis 330 running nasal to temporal, as shown in FIG. 3 (ii) and FIG. 3 (iv), no overlap region 4 arises. Such a capsulotomy incision 1 could only be executed as a closed incision if it had its starting point 2 as well as its ending point 3 extended in the same manner beyond 360°, with a direction of progress of the macroscopic scanning pattern 145 running parallel to an axis running nasal to temporal.

If the expected direction of movement and thus the direction of offset is known a priori, this simple measure can be used to obtain guaranteed closed cuts. The starting point 2 and/or ending point 3 of the two macroscopic scanning patterns 145 must then be selected on a section of the incision line which extends substantially in the direction in which the movement of the patient's eye 310 is expected.

In a capsulotomy of the eye lens of the patient 350, a movement of the lens is expected in the superior inferior direction that is, the head-to-foot axis, due to, for example, the respiration of the patient (see Eur J Ophthalmol 2015; 25 (2): 112-118; T. Schultz, S. C. Joachim, I. Tischoff, H. B. Dick: "Histologic evaluation of in vivo femtosecond laser-generated capsulotomies reveals a potential cause for radial capsular tears").

A starting point 2 of the macroscopic scanning pattern 145 in a region of the capsulotomy incision 1 in which the direction of progress of the macroscopic scanning pattern 145 runs parallel to an axis which runs superior to inferior, together with an extension of the incision line beyond 360°, can in this case lead to an effective guarantee that the incision is closed. The increase in the angle beyond 360° must be at least 180° u/π/r in this case, where r is the radius of the circular path and u is the offset.

Figure 4A:
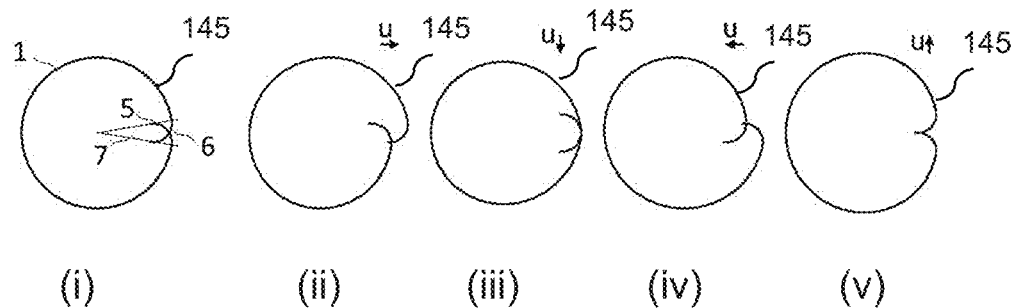
FIGS. 4A and 4B depict a capsulotomy incision containing an overlapping structure which is formed by inner hooks in an overlap region, the effects of different offset directions, and the calculation of the optimal hook structure.

FIG. 4A depicts a capsulotomy incision 1 which includes an overlapping structure 5, 6, which is formed by inner hooks, in an overlap region 4, as well as the effects of different offset directions. In this case, the incision line and/or the closed sectioned area is extended by hook-like overlapping structures 5, 6 in the region of the starting point 2 and also the ending point 3 of the macroscopic scanning pattern 145, since when a capsulotomy incision 1 is made, the capsular bag of the eye lens of the patient's eye 310 is sectioned in its full depth so as to obtain a circular opening. If the hooks are routed to the inside of the enclosed area, additional incisions are created in the interior, but the exterior essentially retains its shape. This is advantageous if the integrity of the outer area is to be maintained for example, when a hole will be cut, and the removed piece in the space of the hole need not remain in-tact, but the edge of the hole does need to be preserved.

Smaller arc-shaped "hooks" 5, 6 in the region of the starting point 2 and of the ending point 3 of the macroscopic scanning pattern 145 of the incision line of the capsulotomy incision 1 re-establish the closed form of the incision line if there is an offset u which can be caused by a movement of the patient's eye 310 relative to the ophthalmic laser treatment device during the execution of the capsulotomy incision 1 in different directions; see FIG. 4*a* (ii), (iii), (iv), (v), as compared to such an incision without offset, as in FIG. 4*a* (i). A circle segment with a radius u in this case represents the minimal extension of the incision, and consequently the macroscopic scanning pattern 145, which allows for a movement by u in a direction which is not determined in advance. An angular range 7 of the intended incision line and/or its macroscopic scanning pattern 145 need not be incorporated, due to the expansion of the hook, without compromising the closed form.

Figure 4B:
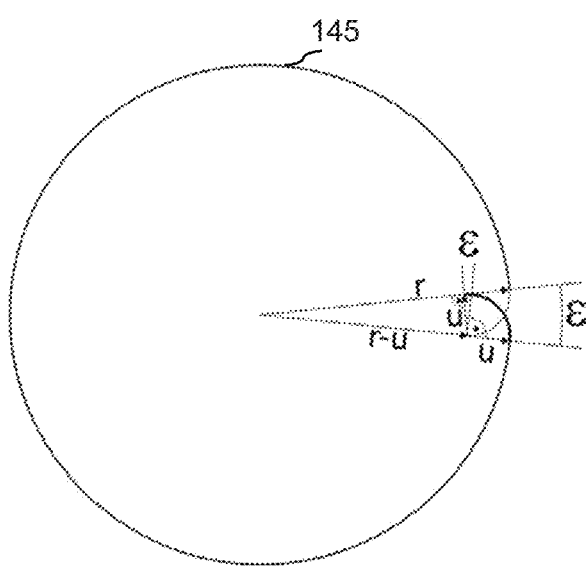

FIG. 4B describes the calculation of the optimum hook structure 5, 6 that is, an advantageous design of the circular arc-shaped hooks for an intended circular, closed incision such as the capsulotomy incision 1. In a sector of the angular range 7 with the angle ε around the starting point 2 and/or the ending point 3 of the macroscopic scanning pattern 145 of the circular incision, the intended circular path is replaced by smaller circular sectors which hooks 5, 6 with the radius u, wherein u is the offset which must be bridged during the execution of the capsulotomy incision 1. The size of the angular range is calculated as ε=arcsin(u/r−u)

The hooks 5, 6 extend over an angular range of 90°+ε about a center point which is r−u from the center of the circular capsulotomy incision 1, and is located on the arms of the sector of the angular range 7 with the angle ε. The hooks 5, 6 open into the circular capsulotomy incision 1 with the same tangents, and nestle against the arms of the sector ε. The resulting incision line and/or its macroscopic scanning pattern 145 has no spikes which point into the tissue material surrounding the hole. For the capsulotomy incision in the patient's eye 310, this leads to a high load capacity of the hole edge, which is desired at that point.

Figure 4C:
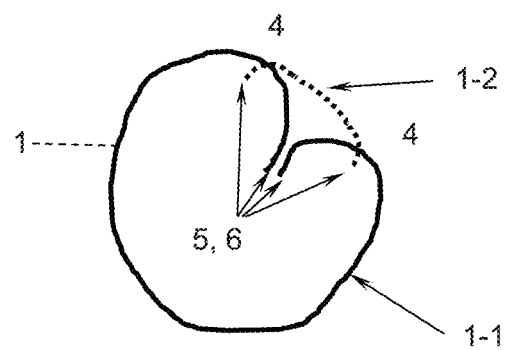
FIGS. 4C and 4D depict a capsulotomy incision containing two overlap regions.
Figure 4D:
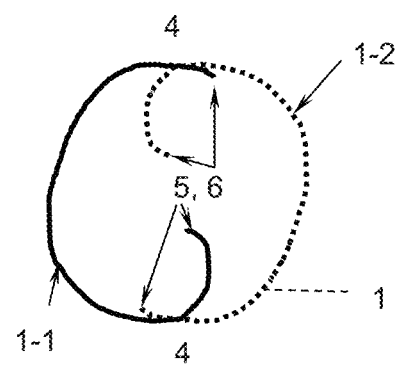

FIGS. 4C and 4D illustrate two variants of capsulotomy incisions 1, each containing two overlap regions 4. The closed incision FIG. 1 which is ultimately obtained is made up of two non-closed partial incision figures which overlap in two overlap regions 4 near their starting points and ending points, respectively, of their macroscopic scanning pattern 145. This can support the execution of a circular incision figure of the capsulotomy incision 1, which is advantageous for improving the centering of the intraocular lens inserted later into the capsular bag (IOL) for many IOL types.

As such, in a method for performing a capsulotomy incision 1 by means of a short-pulse laser beam of an ophthalmic laser treatment device, an opening can be produced by the focus 130 of a short-pulse laser beam being positioned by means of an x/y-scanning system 411, 412 in its x- and y-focus positions, while a z-scanner 413 provides an oscillating movement in the z-direction, and/or an oscillating movement of the focus 130, which is composed of an oscillation in the z-direction and in a lateral direction, is carried out, while in an x-y plane the desired circular incision figure in this case, the macroscopic scanning pattern of the capsulotomy incision 1, is executed slowly.

In the case of the incision figures in FIGS. 4C and/or 4D, a first non-closed curve 1-1 of a macroscopic scanning pattern 145 with a radius r is produced in one step, and a second non-closed curve 1-2 of a macroscopic scanning pattern 145 with a radius r is produced in a second step, and in each case an overlapping structure 5, 6 is produced, which is formed by inner arc-shaped hooks, in the region of the starting point 2 and the endpoints 3 of the macroscopic scanning patterns 145.

In the process, an arc-shaped hook having a radius u is produced as the overlapping structure 5, 6 in the region of the first ending point 3 of the first non-closed curve 1-1 having a radius r, as well as in the region of the starting point 2 of the second non-closed curve 1-2 having a radius r. The two hooks intersect each other in an intended first overlap region 4. Circular hooks with a radius u are again formed as overlapping structures 5, 6, which intersect in a second overlap region 4, in the area of the ending point 3 of the second non-closed curve 1-2, as well as in the area of the starting point 2 of the first non-closed curve 1-1.

The arc-shaped hooks 5, 6 in this case each overlap in the overlap regions 4 in such a manner that the starting points 2 and the ending points 3 of the non-closed curves 1-1, 1-2 are arranged in the interior of a closed incision figure formed by the first and the second non-closed curve 1-1, 1-2 of the capsulotomy incision 1.

Figure 1A:
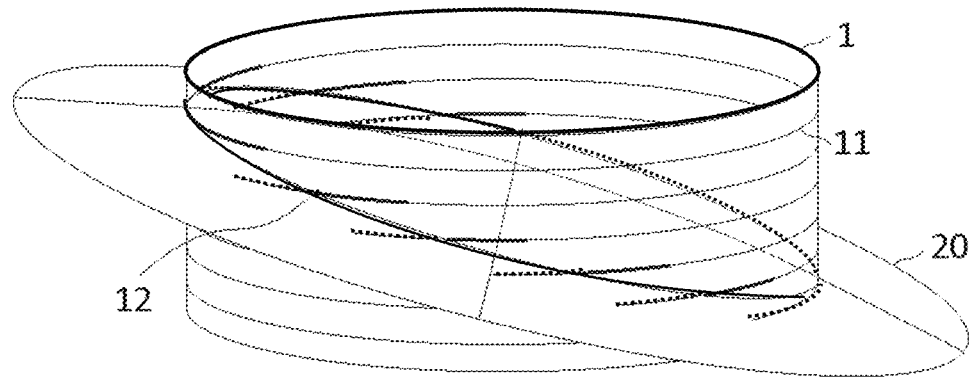
FIGS. 1A and 1B depict a capsulotomy incision according to the prior art, according to a multi-path method, and an offset which occurs during the same due to movements of the patient's eye.
Figure 1B:
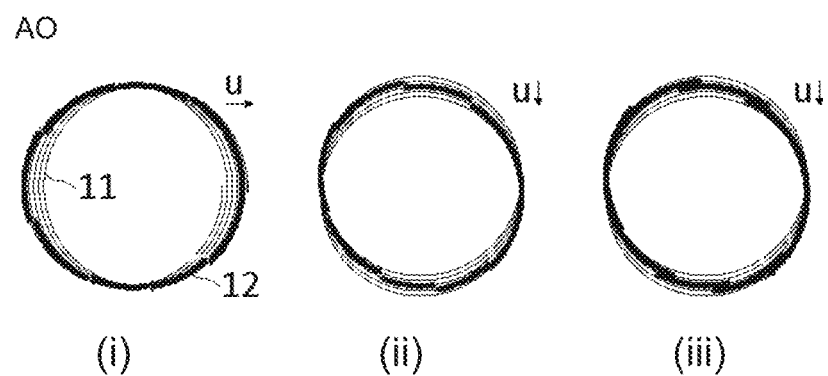
Figure 2A:
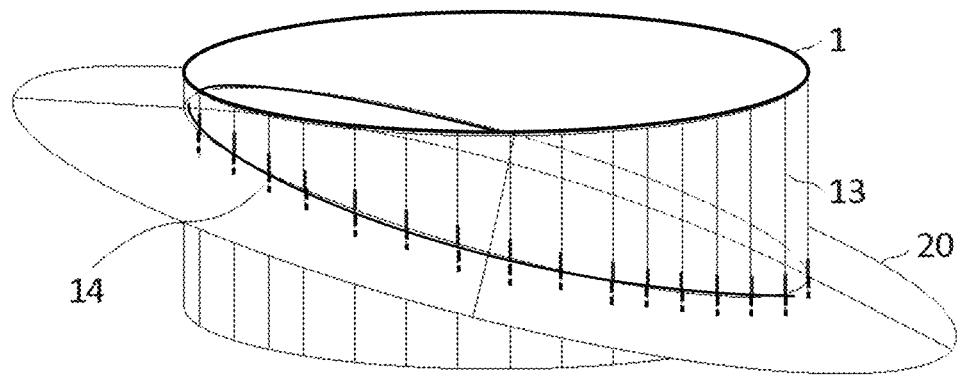
FIGS. 2A and 2B depict a capsulotomy incision according to the prior art, according to a single-path method; and an offset which occurs during the same due to movements of the patient's eye.
Figure 2B:
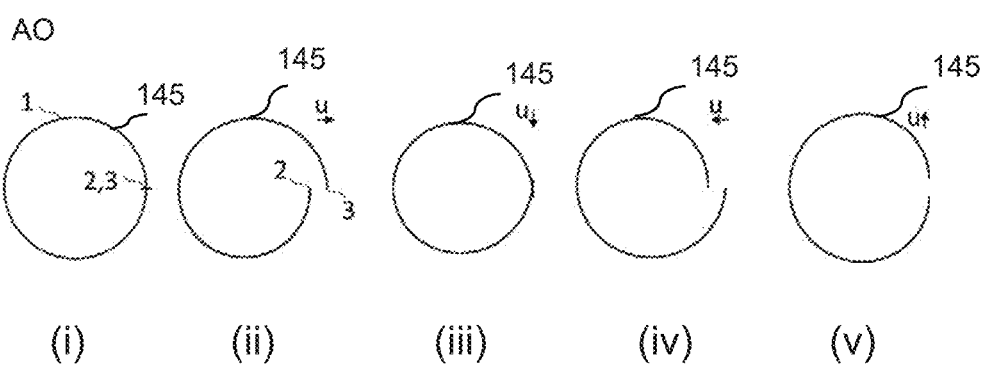

The arc-shaped hooks 5, 6 in the region of the starting point 2 and the ending point 3 of the macroscopic scanning pattern 145 of a closed incision FIG. 1 in a tissue of the eye can also be oriented outward in situations where the integrity of the interior of the incision is more important.

Figure 5A:
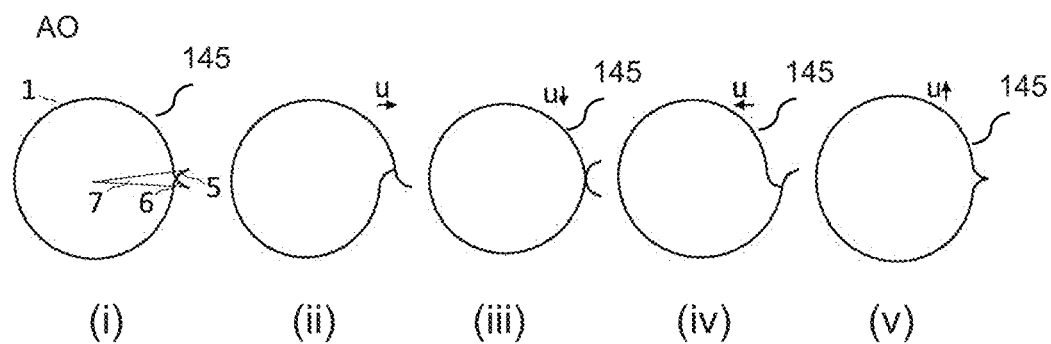
FIGS. 5A and 5B depict a closed incision figure that includes an overlapping structure formed by external hooks in an overlap region, the effects of different offset directions, and calculations of the optimal hook structure.

FIG. 5A shows a macroscopic scanning pattern 145 of a closed incision FIG. 1, which includes an overlapping structure 5, 6, which is formed by outer hooks, in an overlap region 4, as well as the effects of different offset directions. In this case, the macroscopic scanning pattern 145 in this case, that is, the incision line of the closed incision FIG. 1 is likewise extended by hook-like overlapping structures 5, 6 in the region of the starting point 2 as well as the ending point 3 of the macroscopic scanning pattern 145, but in the direction opposite that of the previous example.

The arc-shaped hooks 5, 6 in the region of the starting point 2 and the ending point 3 of the macroscopic scanning pattern 145 of a closed incision FIG. 1 ensure that the incision line is closed when there is an offset u caused by a movement of the patient's eye 310 relative to the ophthalmic laser treatment device during the production of the closed incision FIG. 1 in any direction. An angular range 7 of the macroscopic scanning pattern 145 of the intended incision line in the region of the overlapping structures 5, 6, which forms the overlap region, can be omitted due to the extension of the hooks 5, 6, without compromising the closed form. The outwardly directed hooks 5, 6 increase the integrity of the inner area of the closed incision FIG. 1.

Figure 5B:
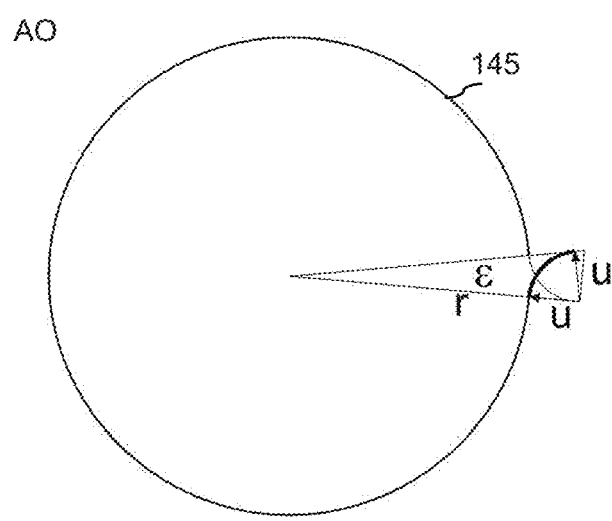

FIG. 5B describes the calculation of the optimum hook structure 5, 6 that is, an advantageous design of the circular arc-shaped hooks for an intended circular, closed incision FIG. 1. In a sector of the angular range 7 with the angle ε around the starting point 2 and/or the ending point 3 of the macroscopic scanning pattern 145 of the circular incision FIG. 1, the intended circular path is replaced by smaller circular sectors, which hooks 5, 6 with the radius u, wherein u is the offset which must be bridged. The size of the angular range is calculated as ε=arcsin (u/r+u).

The hooks 5, 6 extend over an angular range of 90°+ε about a center point which is r+u from the center of the circular closed incision FIG. 1 and/or its macroscopic scanning pattern 145, and is located on the arms of the sector of the angular range 7 with the angle ε. The hooks 5, 6 open into the circular incision FIG. 1 with the same tangents, and nestle against the arms of the sector ε.

Figure 6:
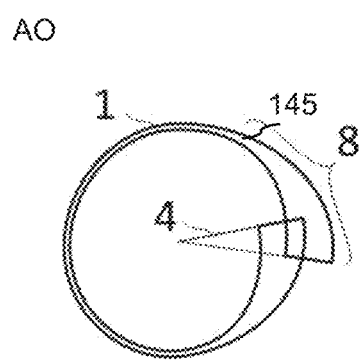
FIG. 6 depicts a capsulotomy incision which includes an overlapping structure which is formed by a broadening of the closed structure in an overlap region.

FIG. 6 illustrates a capsulotomy incision 1 which includes an overlapping structure 8 which is formed by a broadening of the closed incision FIG. 1 in an overlap region 4 in the area of the starting point 2 and/or the ending point 3 of the macroscopic scanning pattern 145.

The incision line of the capsulotomy incision 1 overlaps in an overlap region 4 similarly to the variant of FIG. 3, and is thus produced according to the principles of the capsulotomy incision 1 in FIG. 3. In addition, an intensification of the incision parameters of the focused laser beam in the region of the starting point 2 and/or of the ending point 3 of the macroscopic scanning pattern 145 of this capsulotomy incision 1 result in a broadening of the incision line, which leads to the closing of the incision line even in the event of an offset arising during the execution of the capsulotomy incision 1 due to movements of the patient's eye 310 relative to the ophthalmic laser treatment device.

In the region of the starting point 2 and/or of the ending point 3 of the macroscopic scanning pattern 145 of the capsulotomy incision 1, the incision intensity is increased, for example by increasing the laser power that is, broadening the effective range of the focus of the laser beam or by a compression of the shot interval of a pulsed femtosecond laser beam that is, a reduction in the spacing of the active areas of the focus of the laser beam such that the incision can grow together and close even if there is an offset.

Figure 7:
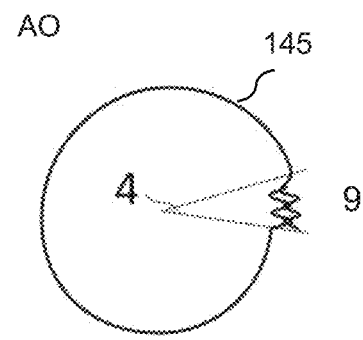
FIG. 7 depicts a capsulotomy incision which includes an overlapping structure formed by meanders in an overlap region.

FIG. 7 again shows a capsulotomy incision 1 which includes an overlapping structure 9 which is formed by a meandering in an overlap region 4. In the overlap region 4 of the macroscopic scanning pattern 145 of the capsulotomy incision 1, the procedure is initially similar to the variant in FIG. 3, and then additional meandering loops are impressed on the macroscopic scanning pattern 145 of the capsulotomy incision 1 in the region of its starting point 2 and/or its ending point 3, which overlap slightly. These then enable a closed connection of the starting point and/or the starting region and the ending point and/or the ending region, even if there is an offset u which arises.

If the intended closed incision FIG. 1 is inclined relative to the horizontal that is, the x-y plane in which a lateral offset u is expected, then care must be taken to construct the overlapping structures, in this case the hooks 5, 6, in three dimensions. So that they still penetrate to the same height i.e., the z-position if there is a lateral offset u, and are therefore connected, it is advantageous if the hook structures 5, 6 are located at the same height and lie horizontal. It is particularly advantageous if the overlap region 4 is realized at points of the macroscopic scanning pattern 145 of the intended closed incision FIG. 1 at which the macroscopic scanning pattern 145 of this incision FIG. 1 does not vary, or varies only slightly, in its height position. This is illustrated in FIG. 8A. The capsulotomy incision 1 of FIG. 8A includes a starting point 2 and an ending point 3 of the macroscopic scanning pattern 145 at the position of a maximum z-coordinate of the macroscopic scanning pattern of the capsulotomy incision 1.

The overlapping structures that is, the hooks 5, 6 are constructed horizontally, although the closed incision FIG. 1 of the capsulotomy incision 1 shown here is inclined from the horizontal. As such, the two hooks 5 and 6 overlap at the same height in a horizontal line 30 when there is any lateral offset u which is smaller than a maximum expected offset, and are thus connected. If the overlapping structures 5, 6 are placed at a position with minimal height variance of the closed incision FIG. 1 in FIG. 8A, this occurs at the position of the maximum z-coordinate of the closed incision FIG. 1, although this would also be possible at a minimum position of the z-coordinate or at plateau points the hooks 5 and 6, even if they still must span a sector ε, can be realized at approximately the same height.

In contrast, FIGS. 8B, 8C and 8D, show a capsulotomy incision 1 which is not parallel to an x-y plane, and which contains an overlapping structure 5, 6 which is formed by inner hooks in an overlap region 4, and which includes a starting and ending point 1, 2 of the macroscopic scanning pattern 145 in a position of the maximum change in the z-direction per unit of time.

In FIG. 8B, the position of the overlapping structure 5, 6 that is, the hooks 5 and 6 is disadvantageously selected at a position of the macroscopic scanning pattern 145 of the closed incision FIG. 1 at which it passes through a strong variance in height. Since the hooks 5, 6 must span a subsector ε of the macroscopic scanning pattern 145 of the closed incision FIG. 1, the hook 5 is higher than the hook 6, and a connection does not result. An inclination of the hooks 5, 6 in the inclined plane of the closed incision FIG. 1 does not help, because the position of the overlap of the overlapping structures 5 and 6 is not known a priori.

If the overlapping structures 5, 6 that is, the hooks 5 and 6 follow the inclination of the closed incision FIG. 1, as shown in FIG. 8C, then there is an overlap in the regions of the starting point 2 and the ending point 3 of the macroscopic scanning pattern 145, even on steeply inclined regions of the closed incision FIG. 1 although with no offset u.

However, if during the incision an offset d arises, as illustrated in FIG. 8D, the height offset within the overlapping structures 5, 6 leads to a loss of the spatial overlap of the two overlapping structures 5, 6, although the overlapping structures 5, 6 still overlap laterally when viewed from above. A construction of the overlapping structures 5, 6 at the same height z is therefore advantageous.

Because the z-advancement per unit of time varies if the overlapping structures 5, 6 are constructed horizontally, if the overlapping structures 5, 6 are constructed in a region of the closed incision FIG. 1 which is not horizontal, high accelerations of the z-advancement movement are required. In order to avoid this as well, a placement of the overlapping structures 5, 6, and thus of the starting point and the ending point of the macroscopic scanning pattern 145, at locations with low to no z-variation i.e., at maxima, minima and/or saddle points is advantageous.

Figure 9A:
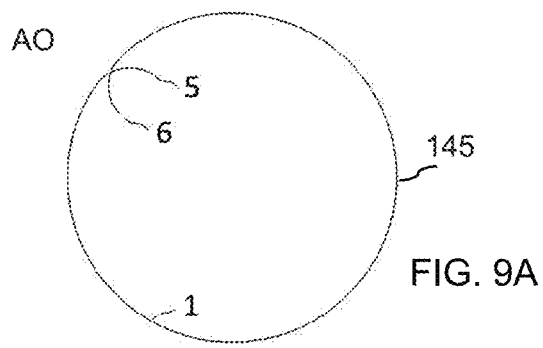
FIGS. 9A and 9B depict a capsulotomy incision which is not parallel to an x-y plane, which includes an overlapping structure which is formed by inner hooks in an overlap region, and a starting and ending point of the macroscopic scanning pattern at a maximum z-coordinate of the scanning pattern of the capsulotomy incision, with identification of the principal (microscopic) scanning pattern of a single-path incision.
Figure 10A:
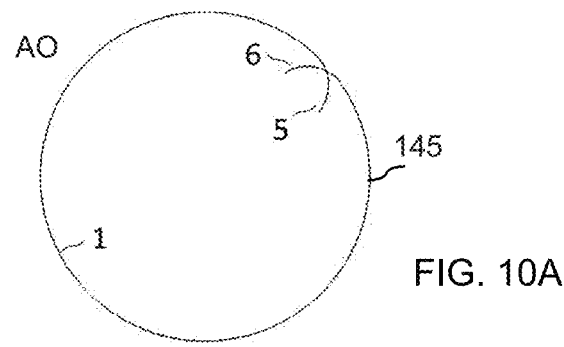
FIGS. 10A-10C depict a capsulotomy incision which is not parallel to an x-y plane, which includes an overlapping structure which is formed by inner hooks in an overlap region, and a starting and ending point of the macroscopic scanning pattern at a position of the maximum change in the z-direction per unit of time, with identification of the principal (microscopic) scanning pattern of a single-path incision.
Figure 9B:
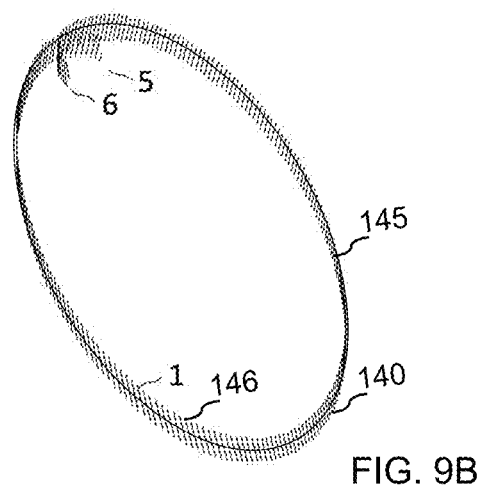
Figure 10B:
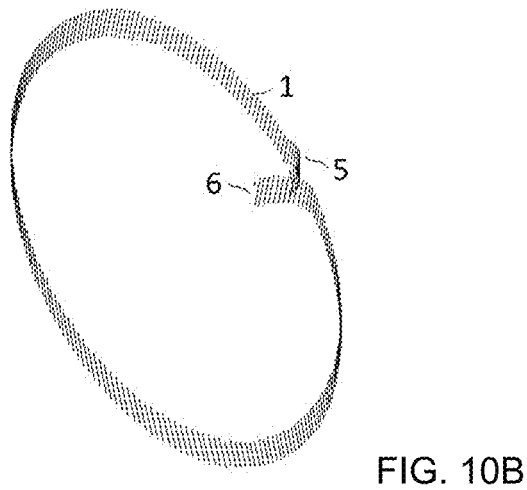
Figure 9C:
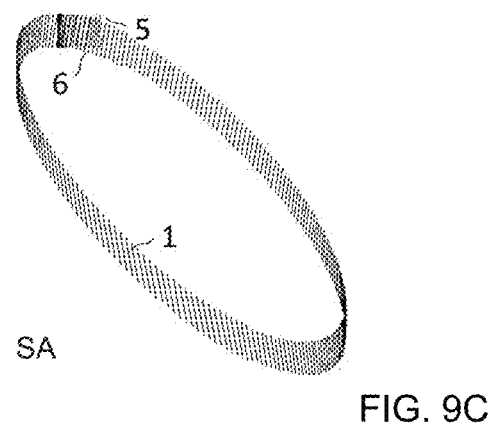
FIG. 9C depicts a circular capsulotomy incision which does not run parallel to an x-y plane and which includes an overlapping structure which is formed by inner hooks in an overlap region, and a starting and ending point of the macroscopic scanning pattern at a maximum z-coordinate of the scanning pattern of the capsulotomy incision, with identification of the principal (microscopic) scanning pattern of a single-path incision in a side view.
Figure 10C:
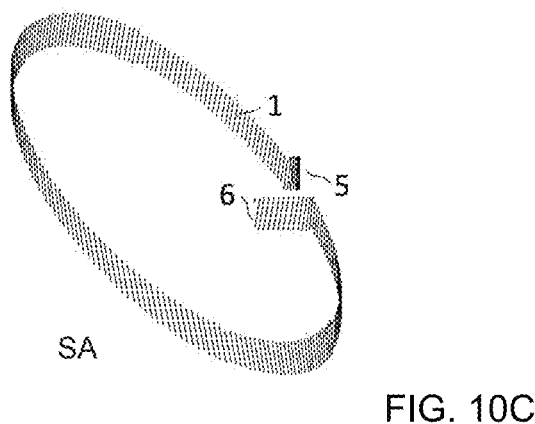

FIGS. 9A-9C, as well as FIGS. 10A-10C, show a circular capsulotomy incision FIG. 1 which does not run parallel to an x-y plane, in a top view AO (FIGS. 9A and 10A), a perspective view (FIGS. 9b and 10b), and a side view (FIGS. 9C and 10C) having an overlapping structure which is formed by inner arc-shaped hooks 5, 6 in an overlap region 4. Both the capsulotomy incision 1 of FIGS. 9A-9C and the capsulotomy incision 1 of FIGS. 10A-10C are produced using a single-path method.

The figures in perspective view and inside view show the details of a scanning pattern 140 of this capsulotomy incision 1, in which an oscillating movement of the focus 130 is carried out which is composed of an oscillation in the z-direction and in a lateral direction, while the circular macroscopic scanning pattern 145 of the capsulotomy incision 1 is made in an area which runs with an incline to the x-y plane. In the figures, tracks 146 that is, adjacent straight incision lines of the scanning pattern, also called strokes or slashes, by which the incision area 1 is swept, are not executed exactly vertically. This is due to the composite oscillation of the focus of the laser beam made up of an oscillation in the z-direction and in a lateral direction by an oscillatory movement of the z-scanner 413 and at least one lateral scanner 411, 412 used in this case.

The capsulotomy incision 1 of FIGS. 9A-9C in this case has a starting point and an ending point of the macroscopic scanning pattern 145 at a maximum z-coordinate of the macroscopic scanning pattern 145 of the capsulotomy incision 1. The capsulotomy incision 1 of FIGS. 10A-10C, however, includes a starting point and an ending point of the macroscopic scanning pattern 145 at a position of maximum change in the z-direction per unit of time of the scanning pattern of the capsulotomy incision 1 in other words on the flanks of the inclined capsulotomy incision 1.

If the starting point and the ending point of the macroscopic scanning pattern 145 of the capsulotomy incision 1 are placed on the flanks of the oblique incision figure, a height offset can prevent overlapping of the overlapping structures 5, 6, which is best seen in FIG. 10C. However, if the starting point and the ending point of the macroscopic scanning pattern 145 of the capsulotomy incision 1 are made at a location with minimal height variation and/or optimally without height variation, an overlap of the overlapping structures i.e., the arc-shaped hooks 5, 6 is ensured, which can be seen in FIG. 9C.

Figure 11:
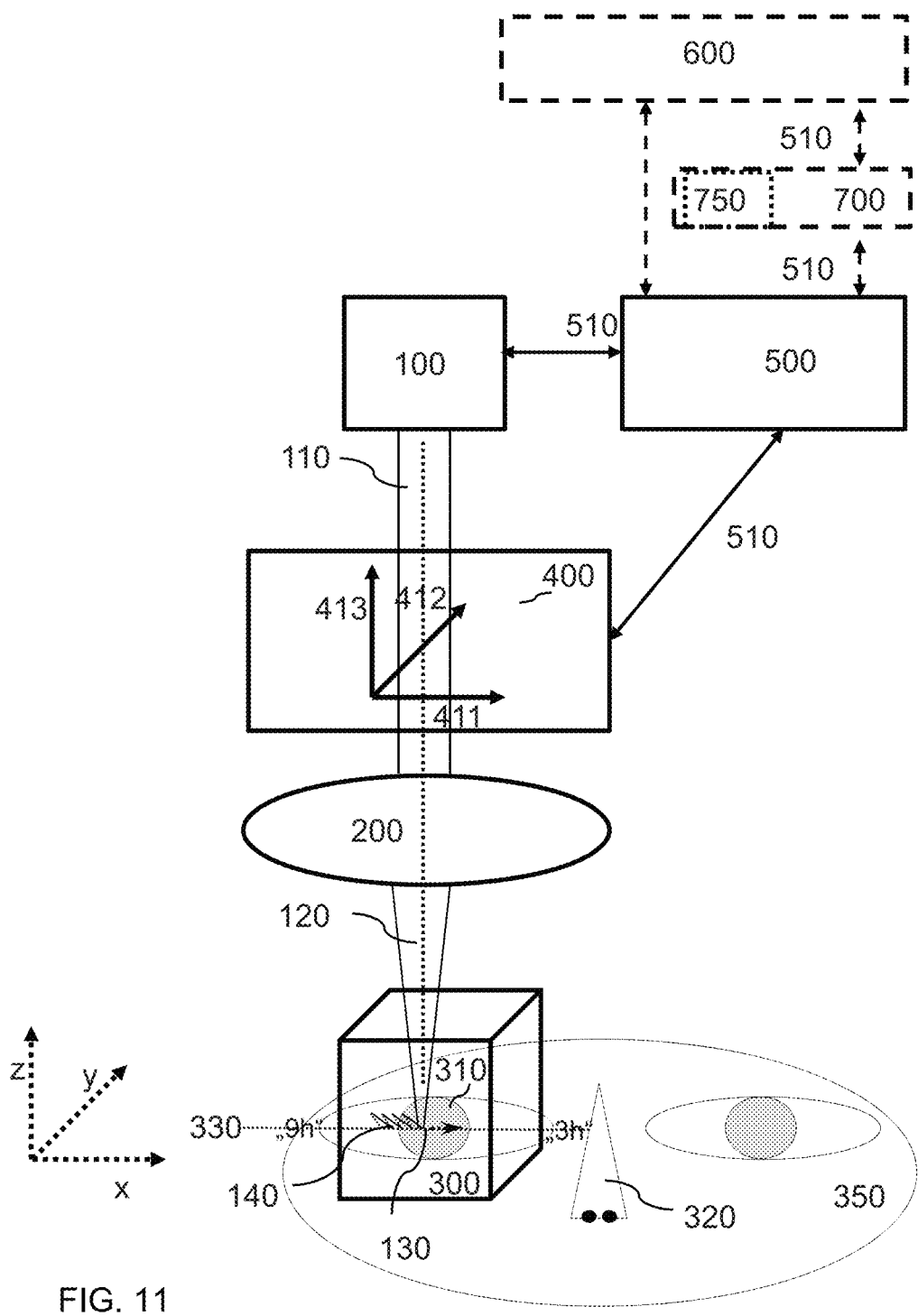
FIG. 11 depicts a first example embodiment according to the invention of an ophthalmic laser treatment device.

FIG. 11 shows a first example embodiment of an ophthalmic laser treatment device and its interaction with a planning device 700 according to the invention.

The ophthalmic laser treatment device includes a device for generating 100 a laser beam which comprises a femtosecond laser having a wavelength in the range of 1020-1060 nm. The pulse duration of this femtosecond laser is 500-600 fs; the pulse energy is about 10 µJ.

Furthermore, the laser treatment device includes an optical system 200 for focusing the laser beam in a focus 130, with a numerical aperture of 0.2, which has a frame size of about 6 mm. With this arrangement, it is possible to reach a processing volume 300 of 6 mm×6 mm×6 mm, in which a portion of a patient's eye 310 can be placed, the tissue of which will be processed by application of the focused laser beam 110 of the femtosecond laser. The optical axis 120 runs parallel to the z-direction.

The ophthalmic laser treatment device shown here further includes a device for changing the position 400 of the focus 130 with a scanning system of three scanners 411, 412, 413, which can perform scanning movements in the x, y and z directions, and which can perform a scanning movement and thus a movement of the focus of the laser beam 110 in any direction by linking these scanning movements. The scanning system advantageously comprises a fast scanning system with three fast scanners which can execute fast scanning movements in the x, y or z directions, and a slow scanning system with three slow scanners which can execute slow scanning movements in the x, y or z direction (not shown in the figure). A scanning pattern 140 can be traversed by the cooperation of the fast and slow scanning systems.

Furthermore, the arrangement includes a one-piece central control system 500 which is connected via communication channels 501 to the device for generating 100 a laser beam that is, the femtosecond laser system and to the device for changing the position 400 of the focus 130, and is adapted to control both the femtosecond laser system and also all scanners 411, 412, 413 of the device for changing the position 400 of the focus 130, and optionally also the optical system 200.

The ophthalmic laser treatment device communicates in this example embodiment with an external characterization device 600, with which it is connected through wireless communication channels 510. In the example embodiment described here, the same is a device for optical coherence tomography (OCT), by use of which structural parameters of the patient's eye 310 are determined before the laser treatment is carried out. In this case, the ophthalmic laser treatment device can optionally transmit a request for the determination of structural parameters of the patient's eye to the characterization device 600.

The structural parameters determined by the characterization device 600, such as the location of boundaries of the various ocular tissues, such as the position of the eye lens, are transmitted by the characterization device 600 to a planning device 700 according to the invention, again via wireless communication channels 520. The planning device according to the invention includes a selection table 750 of scanning patterns 140 of closed structures 1 in the tissues of an eye. The structural parameters obtained from the characterization device 600 are evaluated in the planning device 700, and the automatic selection of a scanning pattern 140 from the selection table 750 occurs based on the result of this evaluation. This is transmitted to the control device 500 of the ophthalmic treatment device, and can therefore be used to produce the desired scanning pattern 140 of the closed structure 1 in a tissue of the patient's eye 310.

Figure 12:
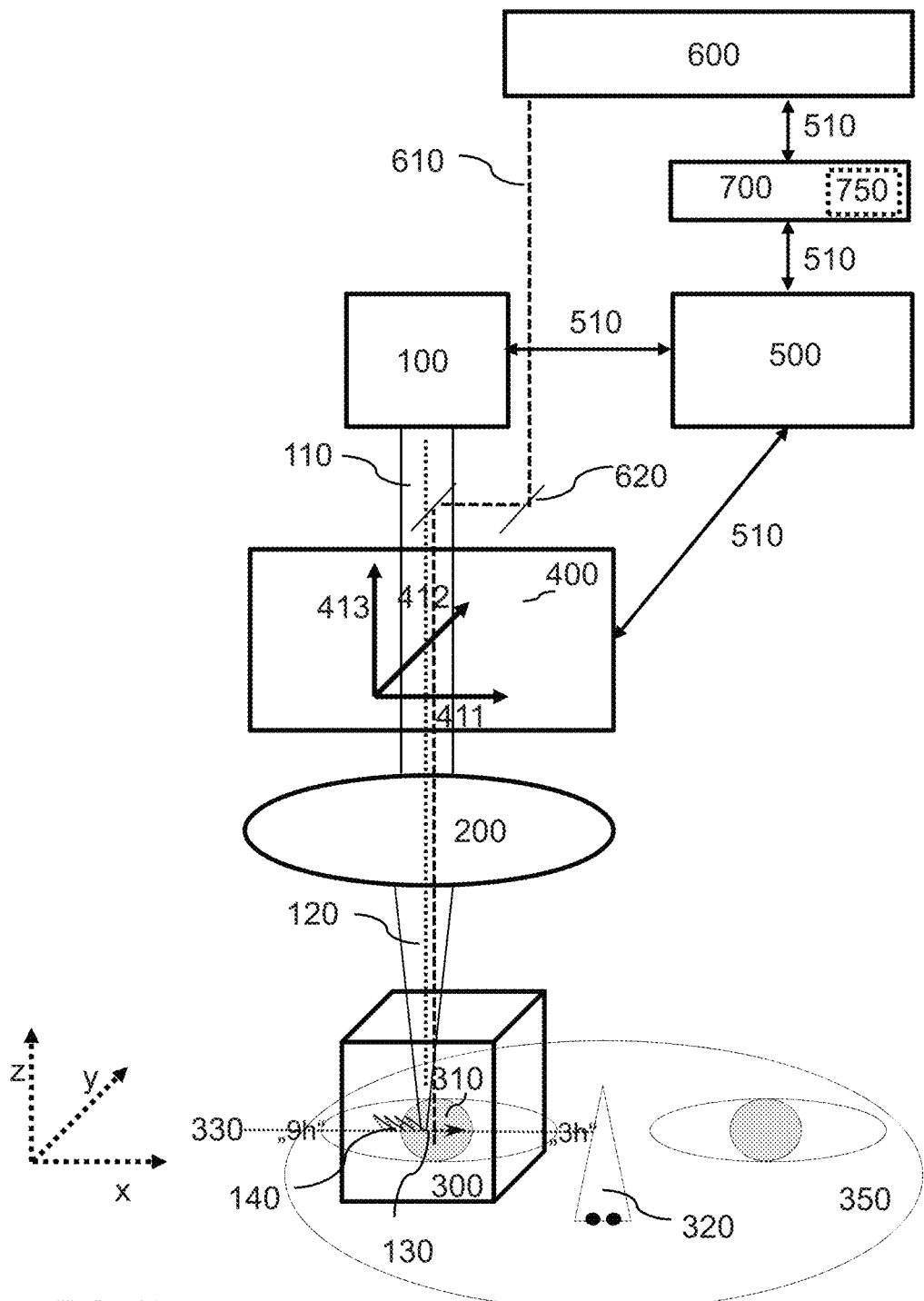
FIG. 12 depicts a second example embodiment according to the invention of an ophthalmic laser treatment device.

FIG. 12 shows a second example embodiment of an ophthalmic laser treatment device according to the invention. This laser treatment device corresponds to that of the first example embodiment. However, in the second example embodiment, both the characterization device 600 in this case, a device for optical coherence tomography (OCT) and the planning device 700 are integrated into the ophthalmic laser treatment device. The communication channels 510 between the individual components are all implemented in this case by cable connections.

The planning device 700 in this case also contains a selection table 750 of scanning patterns 140 of closed structures 1. In addition, an algorithm for creating a scanning pattern 140 of a closed structure 1 is encoded into the planning device 700, by use of which such a scanning pattern 140 can be produced completely freely and independently of the scanning patterns 140 contained in the selection table 750, and/or a scanning pattern 140 in the selection table 750 can be modified.

In contrast to the ophthalmic laser treatment device of the first example embodiment, in this case, structural parameters of the patient's eye 310 can be determined after the fixing of the patient's eye 310 by use of a patient interface to the ophthalmic laser treatment device and/or to a corresponding laser applicator of the ophthalmic laser treatment device, which is not shown here, with the aid of a characterization beam 610. These structural parameters are transmitted to the integrated planning device 700, which creates a corresponding scanning pattern 140 to produce the closed structure 1. This scanning pattern 140 is then passed to the control device 500, and used by the latter for controlling the production of the corresponding structure in the patient's eye 310 by a focus movement of the treatment laser beam along the scanning pattern 140.

The integration of the characterization device 600 and the planning device 700 significantly simplifies a corresponding treatment process, since the characterization device 600 can be used even during the production of the structures in the patient's eye. In addition, a determination of structural parameters of the eye is possible in the fixed state—by way of example, a conversion of structural parameters of a non-fixed patient's eye 310 into structural parameters of a fixed patient's eye 310 is omitted in this case.

The features of the invention mentioned above and explained in various example embodiments can be used not only in the exemplified combinations but also in other combinations, or alone, without departing from the scope of the present invention.

A description of a device which refers to a method feature applies with respect to these features analogously for the corresponding method, while method features accordingly represent functional features of the described device.

The invention claimed is:

1. A planning device for planning a scanning pattern of a closed structure to be created by control of an ophthalmic laser treatment apparatus that when operated produces the closed structure in a tissue of a patient's eye in a single-pass method, the planning device comprising:
 a controller processor;
 memory operably coupled to the controller processor in which is encoded a selection table of scanning patterns, an algorithm for creating a scanning pattern of the closed structure or both of the foregoing;
 the memory storing executable instructions that when executed cause the planning device to define a change over time in a position of a focus of a laser beam of the ophthalmic laser treatment apparatus in the tissue of the patient's eye by the scanning pattern with reference to the three spatial axes x, y, and z;
 wherein the scanning pattern comprises a macroscopic scanning pattern of the closed structure to be created by control of the ophthalmic laser apparatus;
 wherein the z-direction runs parallel to an optical axis of the ophthalmic laser treatment device;
 wherein a starting point of the macroscopic scanning pattern of the closed structure in the tissue of the patient's eye is fixed in a region of a minimum change in the macroscopic scanning pattern in the z-direction per unit of time, or in a region in which a direction of progress of the macroscopic scanning pattern runs parallel to a direction of a maximum offset in an x-y plane by movements of the patient's eye relative to the ophthalmic laser treatment device during an ophthalmic laser treatment.

2. The planning device according to claim 1, further wherein the memory stores executable instructions that when executed cause arranging a starting point of the macroscopic scanning pattern of the closed structure in a region in which the direction of progress of the macroscopic scanning pattern runs parallel to an axis of the patient's eye which runs superior to inferior, or in a region of a minimum or maximum z-coordinate ($z_{min}$, $z_{max}$) of the macroscopic scanning pattern of the closed structure.

3. The planning device according to claim 2, further wherein the memory stores executable instructions that when executed cause the macroscopic scanning pattern to include an overlapping structure in an overlap region at the starting point and/or at an ending point of the macroscopic scanning pattern of the closed structure.

4. The planning device according to claim 3, further wherein the memory stores executable instructions that when executed cause an advancement of the starting point and/or an extension of the ending point of the macroscopic scanning pattern beyond the actual location of the ending point, and/or broadening the closed structure in the overlap region at the starting point and/or at the ending point of the macroscopic scanning pattern, and/or a meandering in the overlap region at the starting point and/or at the ending point of the macroscopic scanning pattern, and/or hook-like regions which point into the closed structure or out of the closed structure in the overlap region at the starting point and at the ending point of the macroscopic scanning pattern of the closed structure.

5. The planning device according to claim 4, further wherein the broadening of the closed structure in the overlap region at the starting point and/or at the ending point of the macroscopic scanning pattern is done by a change in a power of the laser beam or by a reduction in a rate of change of the position of the focus.

6. The planning device according to claim 4, further wherein the memory stores executable instructions that when executed cause the hook-like regions to be produced as a function of the maximum expected offset ($u_{max}$).

7. The planning device according to claim 4, further wherein the memory stores executable instructions that when executed cause a maximum expected offset in the x-y plane, and that the hook-like regions are produced by circular arcs with a radius u, which corresponds to the amount of the maximum expected offset ($u_{max}$) in the overlap region.

8. The planning device according to claim 3, further wherein the memory stores executable instructions that when executed cause the closed structure to be composed of at least two non-closed sub-structures, and has at least two overlap regions.

9. The planning device according to claim 1, further wherein the memory stores executable instructions that when executed cause assigning of additional parameters of the laser beam to the scanning pattern (140).

10. The planning device according to claim 1, further wherein the memory stores executable instructions that when executed cause the closed structure to be determined by characterization data of the patient's eye, which is collected by a characterization device that collects structural data of the patient's eye by optical coherence tomography (OCT), by a Scheimpflug camera, by confocal detection, or by ultrasound.

11. An ophthalmic laser treatment device, comprising:
 a planning device according to claim 1;
 a device for generating a laser beam;
 an optical system for focusing the laser beam in a focus in a working volume; and
 a device for changing the position of the focus in the working volume, which can be described with three spatial directions x, y and z;
 wherein the controller processor is further configured for controlling the laser treatment device.

12. The ophthalmic laser treatment device according to claim 11, further comprising a characterization device for generating characterization data of the patient's eye.

13. The ophthalmic laser treatment device according to claim 11 wherein the characterization device comprises an optical coherence tomography (OCT) device, a confocal detector, a Scheimpflug camera, or an ultrasound device.

14. The ophthalmic laser treatment device according to claim 11, wherein the device for generating a laser beam, generates a pulsed femtosecond laser beam and the closed structure includes a closed incision figure.

15. The planning device according claim 1, wherein the memory stores executable instructions that when executed cause a closed structure to be formed corresponding to a capsulotomy incision.

16. The planning device according to claim 1, wherein the scanning pattern intersects itself proximate the starting point.

17. A planning device for planning a scanning pattern of a closed structure to be created by control of an ophthalmic laser treatment apparatus that when operated produces the closed structure in a tissue of a patient's eye in a single-pass method, the planning device comprising:
a controller processor;
memory operably coupled to the controller processor in which is encoded a selection table of scanning patterns, an algorithm for creating a scanning pattern of the closed structure or both of the foregoing;
the memory storing executable instructions that when executed cause the planning device to define a change over time in a position of a focus of a laser beam of the ophthalmic laser treatment apparatus in the tissue of the patient's eye by the scanning pattern with reference to three spatial axes x, y, and z;
wherein the scanning pattern comprises a macroscopic scanning pattern of the closed structure to be created by control of the ophthalmic laser apparatus; and
wherein a starting point of the macroscopic scanning pattern of the closed structure in the tissue of the patient's eye is arranged in a region in which an angle between a direction of progress of the macroscopic scanning pattern and a direction of maximum offset caused by movements of the patient's eye relative to the ophthalmic laser treatment device during an ophthalmic laser treatment is minimized.

18. The planning device according to claim 17, wherein the scanning pattern intersects itself proximate the starting point.

19. A method for planning a scanning pattern of a closed structure to be created by control of an ophthalmic laser treatment device that when operated produces the closed structure in a tissue of a patient's eye in a single-pass method, the method comprising:
providing a controller processor operably coupled to a memory;
describing the scanning pattern such that a change over time of a position of a focus of a laser beam of the ophthalmic laser treatment device in the tissue of the patient's eye, with respect to the three spatial axes x, y, and z is made;
describing the scanning pattern such that the scanning pattern contains a macroscopic scanning pattern of the closed structure to be created by control of the ophthalmic laser apparatus; and
selecting the scanning pattern from a selection table of scanning patterns stored in the memory or creating the scanning pattern by application of an algorithm stored in the memory, wherein:
a starting point of the macroscopic scanning pattern of the closed structure in the tissue of the patient's eye is fixed in a region in which an angle between a direction of progress of the macroscopic scanning pattern and a direction of a maximum offset ($u_{max}$) caused by movements of the patient's eye relative to the ophthalmic laser treatment device during an ophthalmic laser treatment is minimal.

20. The method according to claim 19, further comprising describing the scanning pattern such that the scanning pattern intersects itself proximate the starting point.

21. A method for planning a scanning pattern of a closed structure to be created by control of an ophthalmic laser treatment device that when operated produces the closed structure in a tissue of a patient's eye in a single-pass method, the method comprising:
providing a controller processor operably coupled to a memory;
describing the scanning pattern such that the scanning pattern describes a change over time of a position of a focus of a laser beam of the ophthalmic laser treatment device in the tissue of the patient's eye, with respect to the three spatial axes x, y, and z;
wherein the z-direction runs parallel to an optical axis;
wherein the scanning pattern contains a macroscopic scanning pattern of the closed structure to be created by control of the ophthalmic laser apparatus; and
selecting the scanning pattern from a selection table of scanning patterns stored in the memory or is creating the scanning pattern by application of an algorithm stored in the memory, wherein:
a starting point of the macroscopic scanning pattern of the closed structure in the tissue of the patient's eye is fixed in a region of a minimum change in the macroscopic scanning pattern in the z-direction per unit of time, or in a region in which a direction of progress of the macroscopic scanning pattern runs parallel to a direction of a maximum offset ($u_{max}$) in an x-y plane by movements of the patient's eye relative to the ophthalmic laser treatment device during an ophthalmic laser treatment.

22. The method according to claim 21, further comprising producing an overlapping structure in an overlap region at the starting point and/or at an ending point of the macroscopic scanning pattern of the closed structure.

23. The method according to claim 21, further comprising generating characterization data of the patient's eye, and incorporating the characterization data of a patient's eye manually or automatically to select a scanning pattern from a selection table of scanning patterns or to create a scanning pattern of the closed structure.

24. The method according to claim 21, further comprising taking into account a fixation of the patient's eye to an ophthalmic laser treatment device.

25. A method for producing a closed structure, in which the scanning pattern of a closed structure is planned using a method for planning a scanning pattern of a closed structure according to claim 21, further comprising:
transmitting the scanning pattern of the closed structure to the controller processor, or wherein the controller processor accesses a planning device, which contains the planned scanning pattern of the closed structure, and the control device controls the ophthalmic laser treatment device in such a manner that a focus of a laser beam produces the closed structure in a tissue of a patient's eye.

26. The method according to claim 21, further comprising describing the scanning pattern such that the scanning pattern intersects itself proximate the starting point.

\* \* \* \* \*